United States Patent [19]

Bennett

[11] Patent Number: 4,936,775

[45] Date of Patent: * Jun. 26, 1990

[54] DENTAL ADHESIVE SYSTEM

[75] Inventor: Richard J. Bennett, Milford, Del.

[73] Assignee: Dentsply Research & Development, Corp., Milford, Del.

[*] Notice: The portion of the term of this patent subsequent to Jan. 31, 2006 has been disclaimed.

[21] Appl. No.: 263,641

[22] Filed: Oct. 27, 1988

Related U.S. Application Data

[60] Division of Ser. No. 792,241, Oct. 29, 1985, Pat. No. 4,801,528, which is a continuation of Ser. No. 503,308, Jun. 10, 1983, abandoned, which is a continuation of Ser. No. 259,964, Apr. 4, 1981, abandoned.

[51] Int. Cl.$^5$ .............................................. A61K 5/06
[52] U.S. Cl. ........................................ 433/220; 433/9; 523/116
[58] Field of Search .................... 523/116, 118; 433/9, 433/220, 228

[56] References Cited

U.S. PATENT DOCUMENTS

| | | | |
|---|---|---|---|
| 4,490,115 | 12/1984 | Orlowski et al. | 523/116 |
| 4,491,453 | 1/1985 | Koblitz et al. | 523/116 |

*Primary Examiner*—Veronica P. Hoke
*Attorney, Agent, or Firm*—Woodcock, Washburn, Kurtz, Mackiewicz & Norris

[57] ABSTRACT

Dental cements and abrasives are provided which are polymerizable with visible light. Such adhesives may be applied in thinner films than heretofore possible and demonstrate superior physical properties. Processes employing such materials are disclosed wherein the polymerization of the adhesive is accomplished by transmitting visible light through tooth or other structures to effect the adhesion.

11 Claims, No Drawings

DENTAL ADHESIVE SYSTEM

Related Applications

This application is a division of U.S. application Ser. No. 792,241, filed Oct. 29, 1985 and now U.S. Pat. No. 4,801,528 which is a continuation of Ser. No. 503,308, filed June 10, 1983, now abandoned, which is a continuation of Ser. No. 259,964, filed Apr. 4, 1981, now abandoned.

BACKGROUND OF THE INVENTION

1. Field of the Invention

This invention relates to adhesives. More particularly, this invention relates to polymerizable adhesives useful in dental applications, and to processes for using such dental adhesives. The adhesives of the present invention and the methods of using them find particular utility in bonding crowns, veneers, caps, bridges, repairs and other prostheses to tooth structures. The dental adhesive systems of the invention comprise polymerizable compositions and methods of use in which the compositions may be polymerized by visible light. Such compositions are suitable for through-the-tooth curing so that prosthetic devices may effectively be adhered to tooth structure. Additionally, such adhesives find use in endodontics, orthodontics and other specialized dental and oral applications.

Adhesive compositions useful as dental cements are primarily evaluated by their physical and chemical characteristics. Some of the more important properties include coefficient of thermal expansion, tensile strength, compressive strength, and film thickness required for effective adhesion. Other factors include toxicity, ease of working, and leachability.

It is desirable to select a dental cement having a coefficient of thermal expansion which closely matches the coefficient of thermal expansion of teeth. If the coefficient of thermal expansion of a dental cement is not closely matched to that of the tooth to which it is applied, the normal expansion and contraction of the cement and tooth caused by temperature variations (such as by exposure to hot and cold food and beverage) may cause a cemented prosthesis to detach from the tooth. It is also advantageous to maximize the tensile and compressive strengths of the dental adhesive since the forces to which the tooth and repair structures are exposed during chewing, grinding, or tearing may be quite severe.

It is also desirable to minimize the film thicknesses of adhesive coating materials used in dental applications. Thinner films may effect closer contact between the surfaces to be joined, are less susceptible to erosion by leaching, and are more efficiently cured by visible light polymerization systems. It is also desirable for dental cements to demonstrate toxic acceptability, ease in handling, and minimal leaching.

2. Description of the Prior Art

A variety of organic and inorganic materials have been used as dental cements. Some of the more common ones include: glass ionomer cements such as those which contain aluminosilicopolyacrylic acids, zinc oxyphosphate systems, polycarboxylate cements, and zinc oxide and eugenol mixed with particles of a polymer such as methylmethacrylate. Both chemical and/or mechanical bonding may be involved in such adhesive systems.

Numerous organic materials with or without filler materials have been tried as dental adhesives. U.S. Pat. No. 3,709,866 to Waller, assigned to the assignee of this invention, discloses a two-part photopolymerizable dental composition useful as a dental cement which comprises a monomeric liquid and a catalyst liquid. The monomeric liquid may comprise the hexamethylene diisocyanate adduct of bis-GMA. As used herein the term "bis-GMA" means 2,2-bis[4-(2-hydroxy-3-methacryloxypropoxy)phenyl]propane, also referred to as "diglycidyl methacrylate of bisphenol A". As used herein the term "bisphenol A" means 2,2-bis(4-hydroxyphenyl)propane. The catalyst liquid of the two component system of Waller contains an ultraviolet light sensitive material such as benzoin methyl ether. Use of bis-GMA in dental filling materials and restoratives is described in U.S. Pat. Nos. 3,539,333 to Lee et al and 4,097,994 to Reaville et al.

U.S. Pat. No. 3,835,090 to Gander et al teaches a dental restorative cement comprising a trimethacrylate or triacrylate monomer ester of an aliphatic triol together with bis-GMA and an inorganic filler material in a peroxide-catalyzed system.

U.S. Pat. No. 3,660,343 issued to Saffir, and assigned to the same assignee as this application, discloses a thermosetting epoxy resin hardened with an N-3-oxohydrocarbon substituted acrylamide which may be useful as a dental cement when the addition of filler is no more than 40% based upon the total weight of the composition.

U.S. Pat. No. 4,089,763 to Dart et al teaches a method of repairing teeth using isocyanate modified bisphenol A derivatives and a reducing amine in conjunction with a visible light cured system. Camphoroquinone is described as being the preferred photosensitive component.

European Patent Application No. 0012535 in favor of I.C.I. Ltd. discloses dental compositions comprising a vinyl urethane prepolymer and processes for their manufacture. Substituted norbornane diones are included as photosensitive catalysts.

U.S. Pat. No. 3,677,920 to Kai et al discloses photopolymerizable diisocyanate modified unsaturated polyesters containing acrylic monomers.

U.S. Pat. No. 4,222,835 to Dixon teaches a composition prepared of a liquid vinyl monomer, a UV-activated photoinitiator, a thermal initiator, and an accelerator.

U.S. Pat. No. 4,228,062 to Lee, Jr. et al discloses a rapid setting adhesive of low toxicity having high bond strength to a variety of metals and plastics, and particularly to stainless steel, polycarbonate plastics and tooth enamel. Glycidyl methacrylate is taught as a preferred resin. Conventional peroxide polymerization catalysts are used along with conventional polymerization inhibitors.

Previous dental cements such as those disclosed above have exhibited tensile strengths in the range of 5–20 meganewtons/m$^2$ (Mn/m$^2$), and compressive strengths less than about 200 Mn/m$^2$. Applications of such dental cements have resulted in adhesive layer thicknesses of about 25 microns.

OBJECTS OF THE INVENTION

It is an object of this invention to provide a visible light curable adhesive system which is useful as a dental cement. A further object is to provide such cements having improved tensile strength, which may be utilized as a very thin film, and which are easily workable. Yet another object is to provide such cements which may be quickly cured by a controllable activation step. It is another object of this invention to provide a visible light curable adhesive material and method for its use suitable for use as a dental cement which exhibits greatly increased tensile and compressive strengths. It is a further object of this invention to provide an adhesive system which exhibits greater ease of handling and curing. Another object is to provide methods for the use and application of such cements and adhesives. It is yet another object of this invention to provide adhesives which retain their adhesive and physical effectiveness in reduced film thicknesses. These and other objects are met by the practice of one or more embodiments of this invention.

SUMMARY OF THE INVENTION

The dental adhesive systems of this invention comprise compositions and methods for their use in which the compositions comprise at least one binder resin, at least one diluent monomer, a photoinitiated curing system activated by visible light, and at least one filler material. The compositions of this invention are formulated as one-component systems which exhibit a substantially indefinite practical working time until cured by exposure to visible light, and which may be applied in relatively thin film thicknesses while obtaining improved tensile and compressive strengths. The method of this invention includes adhering a first article to a second article where at least one of the articles is able to transmit visible light. This method is particularly useful for dental applications.

DETAILED DESCRIPTION OF THE INVENTION

The adhesive systems of this invention comprise compositions and methods for their use that are particularly useful in dental applications. The adhesive compositions of this invention comprise a binder resin or resins, one or more diluent monomers, at least one filler material, and a photosensitive curing system which is curable upon exposure to visible light. Optionally coloring agents, opacifiers and/or other modifiers may be included in the adhesive compositions of the invention.

Binder resins which may be used in the compositions of this invention include a wide variety of ethylenically unsaturated polymerizable compositions. Preferably, these resins include acrylated polyesters. Even more preferred are the bis-glycidylmethacrylate adduct of bisphenol A (bis GMA) and its acrylic counterparts. Alternative preferred species include adducts of 2,2,3-trimethylhexane diisocyanate with hydroxyalkyl acrylic species, e.g., hydroxyethyl methacrylate, hydroxypropylmethacrylate, etc. The preferred acrylated polyesters useful in this invention may further be reacted with isocyanates including diisocyanates, to form urethanes useful as binder resins. A wide variety of aliphatic and aromatic isocyanates may be reacted with bis-GMA to form binder resins useful in this invention, such as hexamethylene diisocyanate and phenylene diisocyanate. The most preferred binder resins are the hexamethylene diisocyanate adducts of bis-GMA, such as those disclosed in copending application Ser. No. 182,626, which is assigned to the assignee of this invention and included by reference as if fully set forth herein.

The diluent monomers useful in the practice of this invention may be selected from a wide range of polymerizable monomers capable of sustaining a photochemically initiated polymerization reaction. Preferably the diluent monomer is selected from the group comprising di-, tri-, and higher acrylic species, e.g., ethylene glycol dimethacrylate, diethylene glycol dimethacrylate, triethylene glycol dimethacrylate, etc., trimethylol propane trimethacrylate, and analogs and homologs of such species. Those skilled in the art will appreciate that two or more different binder resins, and/or different diluent monomers may be used in the same system.

The photosensitive curing system (photosensitizing system) used in this invention is selected from those which are activated by exposure to visible light, which are substantially non-toxic for dental applications, and which may initiate rapid and efficient curing. A preferred system comprises the combination of a photosensitive species sensitive to visible light and a reducing agent. The photosensitive species is preferably an alpha diketone (also called an alpha beta diketone). While any alpha diketone capable of initiating polymerization upon exposure to visible light may be used, preferred species include camphoroquinone, and naphthoquinone. Most preferred is camphoroquinone.

The reducing agent of this photosensitizing system are preferably amines. While numerous amines have been found to be useful as reducing agents for alpha diketones, preferred species include tributylamine and tripropylamine. More preferred species include N-alkyldialkanolamines and trialkanolamines. Most preferred is N-methyldiethanolamine.

Unlike many dental cements which do not include filler material, the adhesive compositions used in this system include at least one filler material. Although the function of the filler particles in the adhesive compositions of the invention is not known for certain, and while it is not desired to be bound by any particular theory as to the role played by the filler, it is believed that the filler particles scatter the visible light to which the compositions are exposed thereby facilitating the activation of the light sensitive component of the system. The presence of filler also appears to increase the tensile strength of the adhesive compositions of the invention after they are cured.

The proportion of filler in the adhesive compositions of this invention depends on several factors. Thus, fillers must be selected to ensure a suitable amount of filler to effect a sufficient degree of light scattering to effect efficient curing of the composition and to result in the viscosity and tensile strength desired for a particular application. Such selection must take into consideration the type of filler employed and its particle size distribution. These factors are also balanced against the desire to minimize film thickness in actual use. For example, decreasing the particle size of the filler material to be added to the adhesive composition of this invention results in decreasing the amount of filler material needed to get an adhesive with good tensile and compressive strengths. Also, increasing the amount of filler material added to the adhesive composition increases the viscosity of the adhesive, thus increasing the film thickness that is used. From a consideration of the foregoing those skilled in the art will be able to select filler sizes which will be optimum for a particular application with a particular resin formulation.

Among those fillers which are especially suited for use in this invention are inorganic glasses. Preferred species of glasses include, for example, barium aluminum silicate, lithium aluminum silicate, and strontium, lanthanum, tantalum, etc. glasses. Silica, including submicron silica, or quartz may also be used. The fillers used in the preparation of the adhesive compositions of this invention may be reduced in particle size and then preferably silanated by methods known in the art before they are incorporated into such compositions.

Mixing of the adhesive composition may be achieved using standard compounding techniques. For example, liquids, photoinitiator(s), and accelerator(s) are blended first, and then the fillers are added incrementally thereafter. When blending in the light sensitive portion, however, a photosafe light, i.e., one that does not contain substantial amounts of wavelengths of electromagnetic radiation that would activate the photoinitiating system used, should be employed to avoid initiating polymerization prematurely.

While it is advantageous according to the invention to use photoinitiated one component systems for a dental adhesive because of extended work time, ease in handling and greater control over effecting polymerization, not all wavelengths of electromagnetic radiation are particularily suitable or advantageous for use in dental applications or on human tissue. For example, tooth structure attenuates ultraviolet light sufficiently s that dental adhesives employing photoinitiators sensitive to UV radiation tend to cure only on those portions of the repair exposed directly to the UV light i.e., the edges. It has been found that visible light is much less attenuated by tooth structure and more particularly that visible light having wavelengths of from about 400 nanometers (nm) to about 500 nm can penetrate a substantial distance therethrough. Accordingly, such visible light has been found to be effective when used in conjunction with the photoinitiating systems previously described for use in the practice of this invention.

A wide variety of binder resins, diluent monomers and fillers have been noted as being useful for the practice of one or more embodiments of this invention. As previously suggested, various proportions of each of these components may be used depending on viscosity requirements and/or particle sizes of the filler material. For example, preferred addition levels of filler material with a particle size distribution of from about one to about fifty microns are from about 20% to about 70% based on the total weight of the adhesive composition, with from about 40% to about 70% being more preferable and about 65% being most preferred. If a more finely particulated filler is used, amounts of filler may be decreased due to the relative increase in surface area which attends the smaller sizes of particles.

Formulations for the adhesive compositions may comprise from about 25% to about 80% by weight of a mixture of binder resin and diluent monomer based on the binder resin-diluent monomer-filler components. Where the hexamethylene diisocyanate adduct of bis-GMA is used as the binder resin and triethylene qlycol dimethacrylate is used as the diluent monomer, preferred ranges for the resin/diluent monomer mixture based on the resin-diluent monomer-filler components are from about 25% to about 50% by weight, with the most preferred level being about 35%.

Addition levels of the photoinitiating system useful for the practice of this invention will vary according to the efficiency of the particular system and the wavelengths of electromagnetic radiation chosen to effect curing. In a preferred embodiment, camphoroquinone is used as the photoinitiator in an amount of from about 0.01% to about pb 0.25% based on total weight of the composition, with N-methyldiethanolamine used as the reducing agent in an amount of from about 0.10% to about 0.50%. The wavelength of light employed with such a system is from about 400 nm to about 500 nm.

The adhesive system of this invention may be used to bond two or more articles together. In utilizing the adhesive systems of this invention at least one of the two articles which are to be bonded must be able to transmit the light to be used to initiate polymerization. For example, tooth structure will transmit light having wavelengths of from about 400 nm to about 500 nm and thus may be selected as the transmissive article. If the repair material to be bonded to the tooth is capable of transmitting light having wavelengths within that range, the adhesion between the two surfaces can be substantially complete in a short period of time, e.g., 10 seconds. More extended periods of exposure of the adhesive layer to electromagnetic radiation may be needed, however, if one of the structures to be adhered does not transmit visible light, or if the wavelength of light used is outside the preferred range for the photoinitiating system used. In any event, in practicing the method of the present invention, the adhesive layer is exposed to cure-initiating light for a time sufficient to cause the desired degree of cure of the bonding composition.

In using the adhesive system that is the subject of this invention in the dental field, it is preferred that the tooth structure to be repaired or veneered be preconditioned. This preparation is accomplished by following, to an extent, practices presently employed by those skilled in the art. Thus the surface of the tooth should be cleaned and decayed material removed as needed. The tooth structure is then, preferably, acid etched and an unfilled bonding agent such as Prisma-Bond TM (L. D. Caulk Co.) is preferably applied. The adhesive composition of this invention may then be coated onto the area of the tooth to receive the repair or veneer. The second surface to be brought into contact with the tooth structure, e.g. porcelain, may need preparation, such as a silanating treatment. After such preparation, the second surface is positioned on the tooth surface coated with adhesive. Exposure to electromagnetic radiation of a suitable wavelength is then effected, preferably through the tooth structure, thus polymerizing the adhesive and bonding the tooth structure to the second surface. As noted previously, visible light is less attenuated by tooth structure than is UV light and accordingly, is preferred. A substantially complete seal may be formed over the surfaces being adhered if visible light of a suitable wavelength is used. During the working time one must be careful to work under light that does not activate the photosensitive system used in the adhesive.

It will also be appreciated by those skilled in the art that other adhesive or coating uses may also be found for the compositions of this invention. The only limiting factor is that at least one of the surfaces must be able to transmit visible light. Such uses may include construction or repair of structures made from glass, porcelain, and transparent or translucent plastic materials, for example, Plexiglas ® (Rohm & Haas Co.).

The following examples are given by way of illustration but without limitation. All parts and percentages are by weight unless otherwise noted.

EXAMPLE 1

A rectangular piece of dental porcelain 5×5×2.5 mm, thick, and another piece of porcelain 5×5×2.5 mm. thick, were placed over 4 mm. diameter cavities in a Teflon ® (DuPont Co.) mold. The specimen of dental porcelain was a light shade taken from the Biotone ™ shade guide #59–62. (L. D. Caulk Co.) The cavity in the Teflon ® mold was filled with a composition of cementing consistency (from approximately $1.0 \times 10^6$ centipoise to approximately $1.5 \times 10^6$ centipoise, and more preferably $1.36 \times 10^6$ centipoise, $\pm 0.10 \times 10^6$ centipoise) formulated to contain 35% of a mixture of the hexamethylenediisocyanate adduct of bis-GMA and triethylene glycol dimethacrylate (in a 1:1 ratio), and 65% of finely ground radiopaque barium glass filler (Raysorb T3000, Kimble Div. of Owens-Corning) which had been milled to reduce the particle size and silanated. The particle size distribution of the filler material was about 1–10 $\mu$ with the major portion in the range of about 1–5 $\mu$. Camphoroquinone (Aldrich) was added at a 0.05% level and N-methyldiethanolamine (Pfaltz & Bauer) was incorporated in an amount of 0.17% (based on the weight of the). The tip of a Prisma-Lite ™ (visible light curing unit, Unit #15, light pipe #20 L. D. Caulk Co.) was placed over the porcelain surface and the cementing composition was irradiated through the porcelain for the times provided in Table 1 with light having wavelengths of between 400–500 nm. at an intensity of about 0.4 wt./cm.$^2$/sec. The porcelain was removed and the polymerized slug was taken from the mold. The relatively unpolymerized underside of the slug was successively removed by scraping the material over 120 grit aluminum oxide paper until the sanded surface reached a Barcol hardness of 70; the thickness of the slug of polymerized cement was then measured in mm. The cement was polymerized to depths as shown in Table 1, clearly demonstrating the value of such a luting cement.

TABLE 1

| Example No. | Irradiation Time In Seconds | Depth of Cure Through | | |
|---|---|---|---|---|
| | | Cellophane ≈.1 mm. | Porcelain 1.5 mm | 2.5 mm thick |
| Ex. 1 | 10 | 3.3 | 2.4 | 1.1 |
| | 20 | 4.9 | 3.6 | 2.3 |
| | 40 | 6.5 | 5.2 | 4.1 |

EXAMPLE 2

Denture teeth taken from the Biotone ™ series shades 62, 59, and 65 were ground on their lingual aspects to provide a shell veneer approximately 0.5 mm. thick which completely represented the labial aspect of the teeth involved. These were fitted over a natural tooth of approximately the same shape and cemented to the teeth using the cement of Example 1. The samples were irradiated with the tip of a Prisma-Lite ™ 15–20 for 40 seconds, each tooth receiving 4 irradiations for 10 second intervals. Upon inspection it was subjectively determined by separating the several layers using a Bard-Parker scalpel (blade #25) that the cement was completely hardened, was rigid and was fully polymerized.

EXAMPLE 3

Several successive treatments were made to the shell veneers prepared as in Example 2 and to the enamel surfaces of the natural teeth to which these were cemented using the visible light curable cement of Example 1. In the first instance a coating of prehydrolyzed (using an aqueous 5% acetic acid solution) methacryloxypropyl trimethoxysilane (A 174, from Union Carbide) was coated onto the surface of the porcelain and allowed to dry. In the second step the enamel surface of the tooth was acid etched using a 50% solution of phosphoric acid for 60 seconds. In the third step the treated artificial and natural tooth surfaces were cemented together using the visible light curing cement of Example 1 and the cement was hardened in place by irradiating the labial aspect of the porcelain veneer for 40 seconds using PrismaLite ™ Unit #15/20. At the end of this time it was ascertained that the veneer was well adhered to the tooth.

EXAMPLE 4

A visible light curable composition suitable for use as a dental cement was made by mixing (A) 35.00 grams of a mixture of the hexamethylenediisocyanate adduct of bis-GMA and triethylene glycol dimethacrylate in a 1:1 ratio, (B) 3.00 grams of a silanated fumed silica with an average particle size of 0.04 microns (Aerosil R-972 from Degussa, Inc.), and (C) 62.00 grams of a barium glass (Raysorb T3000 from Kimble Div. of Owens-Corning) which had been milled to reduce particle size and to yield particles ranging from about 1 to about 10 microns, with an average of about 3 microns in size, and silanated with about 3% of methacryloxypropyl trimethoxysilane (A 174) to give an actual silane coating of about 1.1–1.2%. Mixing was continued until a uniform consistency was obtained. Photoinitiators and accelerators were added as in Example 1. The resulting composition contained about 65% solids. American Dental Association Specification 27 (as found in J.A.D.A. 94, 119–1194, June 1977), was used for evaluating tensile strength, resistance to color change under ultraviolet (UV) irradiation, and opacity contrast ratio. Where applicable the specification was followed. Otherwise the 20 mm by 1 mm disc specimens were cured using the molds stated in the ADA Spec. 27 but cured under a photoflood lamp type EBV at a distance of approximately 50 mm from the bulb for 1 minute per side for a total irradiation of 2 minutes. Compressive strength specimens were cured, in 6 mm ID glass tubing stoppered at both ends for 2 minutes, then the tube was rotated 180° and cured for an additional 2 minutes for a total irradiation of 4 minutes. The glass tube was approximately 50 mm from the photoflood bulb. After testing five samples, the average tensile strength was found to be 23.5 Mn/m$^2$. Samples exposed to UV light for 24 hours (ADA Spec 27) exhibited no substantial color change.

The material passed the opacity contrast ratio test as measured using the Munsell chart (Munsell Color Corp., Balt. Md.) and a chip of material 40 mm.×40 mm.×1.6 mm.

Six samples were tested for compressive strength to give an average of 185 Mn/m$^2$. Water sorption tests on three samples gave average values of 0.94 mg/cm$^2$ as measured after one day and 1.17 mg/cm$^2$ as measured after one week. The material had a natural blue white fluorescence.

Radiopacity was evaluated as satisfactory by a test based on ASTM's Standard Test Method for Radiopacity of Plastics for Medical Use (F640-79) as described in *ASTM Test Journal*-79 and a Step Chip Variation to Compare Dental Materials as found in *Brit. Dent. J.*, (1979) 147, pp. 187–188.

The film thickness test is a modification of ADA Specification #30 for Dental Zinc Oxide-Eugenol Type Restorative Materials (JADA, 95, 991–995 (1977)). The procedure is modified as follows:, after allowing the weight to stay on for 10 minutes the PrismaLite ™ is used to irradiate the glass plates for 10 seconds to tack the plates together, after which time the plates are remeasured and film thickness calculated as in section 4.3.5. of Spec. #30.

The cement was polymerized to depths shown in Table 2 using a Prisma-Lite ® 15/62.

TABLE 2

| Example No. | Irradiation Time In Seconds | Depth of Cure |
|---|---|---|
| Ex. 4 | 10 | 3.2 mm. |
|  | 20 | 5.1 mm. |
|  | 40 | >7.2 mm. |

EXAMPLE 5

A visible light curable composition suitable for use as a dental cement was made by mixing 3.5 grams of the resin and diluent monomer mixture as in (A) of Example 4, 0.3 g. of the silanated fumed silica as in (B) of Example 4, 3.10 g. of a silanated barium glass as in (C) of Example 4, and 3.10 g. of a lithium glass (Cer-Vit T1000, from Owens-Corning Fiberglas Corp.) which had been reduced in particle size by milling to yield particle sizes ranging from about 1 micron to about 10 microns. These particles were then silanated with about 3% (A-174). Mixing was continued until a uniform consistency was obtained. The percent of filler materials based on the total weight of the composition and results of tests to evaluate physical properties are listed in Table 3. Curing of the mixture and testing of physical properties were done as in Example 4.

EXAMPLE 6

Example 5 was repeated but with 4.65 g. (46.5%) of the barium glass and 1.55 g. (15.5%) of the lithium glass. Results of tests on physical properties are listed in Table 3. Curing of the mixture and testing of the physical properties were done as in Example 4.

EXAMPLE 7

Example 5 was repeated but with 1.55 g. (15.5%) of the barium glass and 4.65 g. (46.5%) of the lithium glass. Results of tests on physical properties are listed in Table 3. Curing of the mixture and testing of the physical properties were done as in Example 4.

EXAMPLES WITH PIGMENTS

EXAMPLE 8

A visible light curable composition suitable for use as a dental cement was made by mixing 3.28 g. of the resin and diluent monomer mixture as in (A) of Example 4, 0.30 g. of the silanated fumed silica as in (B) of Example 4, 6.20 g. of a silanated barium glass as in (C) of Example 4, 0.11 g. of a white pigmented mixture (5.0% by weight of $TiO_2$ blended with 95% of the same type of resin and diluent monomer mixture used in (A) of Example 4), and 0.11 g. of a yellow pigmented mixture (1% by weight of yellow pigment blended with 99% of the same type of resin and diluent monomer mixture used in (A) of Example 4). Photoinitiators and accelerators were added as in Example 1. Mixing was continued until a uniform consistency was obtained. Curing of the mixture and testing of the physical properties were done as in Example 4.

EXAMPLE 9

A visible light curable composition suitable for use as a dental cement was made by mixing 3.45 g. of the resin and diluent monomer mixture as in (A) of Example 4, 0.30 g. of the silanated fumed silica as in (B) of Example 4, 6.20 g. of a silanated barium glass as in (C) of Example 4, and 0.055 g. of the yellow pigmented mixture as in Example 8. Mixing was continued until a uniform consistency was obtained. Curing of the mixture and testing of the physical properties were done as in Example 4.

EXAMPLE 10

Example 9 was repeated but with 3.39 g. of the monomer mixture and 0.11 g. of the yellow pigmented mixture. Curing of the mixture and testing of the physical properties were done as in Example 4.

I claim:

1. A method of bonding an article to a tooth with a visible light-activated adhesive
   said adhesive comprising binder resin, diluent monomer, initiator for initiating polymerization of said adhesive by exposure to visible light and at least one filler material,
   said method comprising curing said adhesive by irradiation with visible light, such visible light being applied through at least one of said article and said tooth.

2. The method of claim 1 wherein said article is an artificial tooth.

3. The method of claim 1 wherein said article is selected from the group consisting of crowns, veneers, caps, bridges, endodontic articles, and dental prostheses.

4. The method of claim 1 wherein at least a portion of said visible light is transmitted through said tooth.

TABLE 3

| Example No. | Barium Glass | Lithium Glass | Fumed Silica | Irradiation Time With Prisma-Lite 15/062 | Depth Of Cure | Number Of Samples Tested | Average Tensile Strength In Mnt/m² | Average Compressive Strength in Mnt/m² | Film Thickness In Microns |
|---|---|---|---|---|---|---|---|---|---|
| 5 | 31% | 31% | 3% | 10 sec | 3.1 mm. | 5 | 39.6 | 252 | 15 |
|  |  |  |  | 20 sec | 5.8 mm. |  |  |  |  |
|  |  |  |  | 40 sec | 7.2 mm. |  |  |  |  |
| 6 | 46.5% | 15.5% | 3% | 10 sec | 3.0 mm. | 5 | 42.0 | 253 | 12 |
|  |  |  |  | 20 sec | 5.5 mm. |  |  |  |  |
| 7 | 15.5% | 46.5% | 3% | 10 sec | 3.2 mm. | 5 | 39.0 | 237 | — |
|  |  |  |  | 20 sec | 5.4 mm. |  |  |  |  |

5. The method of claim 1 wherein said article comprises porcelain.

6. The method of claim 1 wherein said article is polymeric material capable of transmitting visible light.

7. The method of claim 1 wherein said visible light comprises electromagnetic radiation with wavelengths of from about 400 nm. to 500 nm.

8. The method of claim 1 wherein the adhesive composition comprises by weight at least about 20% of an inorganic filler and said initiator comprises an alpha-diketone and an amine reducing agent.

9. The method of claim 8 wherein said binder resin comprises bis GMA reacted with aliphatic diisocyanate, said alpha-diketone is selected from the group consisting of camphoroquinone, benzil, biacetyl, 9,10-phenanthrene-quinone, and naphthoquinone, said amine is selected from the group consisting of N-alkyldialkanolamine and trialkanolamine, and said filler is selected from the group consisting of inorganic glasses and silica.

10. The method of claim 8 wherein the adhesive composition comprises from about 40% to about 70% of said inorganic filler.

11. The method of claim 1 wherein said adhesive is present in a thickness of less than about 25 microns and the average tensile strength of the cured adhesive bond is greater than about 20 $Mn/m^2$.

* * * * *

UNITED STATES PATENT AND TRADEMARK OFFICE
CERTIFICATE OF CORRECTION

PATENT NO. : 4,936,775
DATED : June 26, 1990
INVENTOR(S) : Richard Bennett

It is certified that error appears in the above-identified patent and that said Letters Patent is hereby corrected as shown below:

| | |
|---|---|
| Col. 4, line 26 | "agent" should be plural --agents-- |
| Col. 5, line 26 | At the end of the line, "s" should be --so-- |
| Col. 7, lines 3 & 4 | "5X5X2.5 mm," should be --5 X 5 X 1.5mm.-- |
| Col. 7, line 24 | "weight of the" should be --weight of the resin--. |
| Col. 7, line 43 | In the column headed "cellophane", the Greek symbol should be -- $\alpha$ --. |
| Col. 7, line 58 | Delete the hyphen in "irradiated-with". |
| Col. 8, line 36 | Change "119-1194" to --1191-1194--. |

Signed and Sealed this

Twenty-ninth Day of October, 1991

Attest:

HARRY F. MANBECK, JR.

*Attesting Officer*  *Commissioner of Patents and Trademarks*